United States Patent [19]
Fujishiro et al.

[11] Patent Number: 5,645,723
[45] Date of Patent: Jul. 8, 1997

[54] PROCESS AND APPARATUS FOR THE EXTRACTION AND PURIFICATION OF DNA

[75] Inventors: Masatoshi Fujishiro; Akio Togashi; Youichiro Tani; Takamaro Ishii, all of Tokyo, Japan

[73] Assignee: Tomy Seiko Co., Ltd., Tokyo, Japan

[21] Appl. No.: 582,700

[22] Filed: Jan. 4, 1996

[30] Foreign Application Priority Data

Aug. 4, 1995 [JP] Japan ................. 7-199391

[51] Int. Cl.$^6$ .......................................... B01D 63/00
[52] U.S. Cl. ................. 210/321.75; 210/321.84; 210/473; 210/416.1; 210/91; 210/134; 210/263; 422/101; 422/119; 422/191
[58] Field of Search ................. 210/651, 416.1, 210/167, 473, 474, 482, 477, 645, 295, 503, 500.26, 660, 257.2, 258, 91, 13.4, 97, 321.75, 321.84, 263; 422/101, 119, 191, 211; 435/7.1; 436/119

[56] References Cited

U.S. PATENT DOCUMENTS

| | | | |
|---|---|---|---|
| 3,883,305 | 5/1975 | Hoskins et al. | 141/130 |
| 4,246,339 | 1/1981 | Cole et al. | 422/101 |
| 4,948,564 | 8/1990 | Root et al. | 422/101 |
| 5,006,309 | 4/1991 | Khalil et al. | 422/101 |
| 5,141,719 | 8/1992 | Ferwood et al. | 210/323.1 |
| 5,167,924 | 12/1992 | Clark | 422/101 |
| 5,273,718 | 12/1993 | Sköjd et al. | 422/101 |
| 5,330,916 | 7/1994 | William et al. | 210/321.63 |
| 5,342,581 | 8/1994 | Sanadi | 422/101 |
| 5,464,541 | 11/1995 | Aysta et al. | 210/767 |

Primary Examiner—Ana Fortuna

[57] ABSTRACT

An object of the present invention is to carry out the extraction and purification of DNA in a short period of time. This object is accomplished by DNA extraction and purification apparatus illustrated in the drawing. This apparatus includes a pipetting unit which can be horizontally moved along a rail by means of a transfer device. This apparatus also includes tube racks which can be moved horizontally and vertically. In these tube racks are disposed filter tubes (not shown) for the extraction and purification of DNA. Moreover, a waste liquid vat and a recovery vat are disposed below these tube racks. The waste liquid vat and the recovery vat are each provided with a suction port (not shown) to be connected to a vacuum pump.

9 Claims, 15 Drawing Sheets

PROCESS AND APPARATUS FOR THE EXTRACTION AND PURIFICATION OF DNA

FIELD OF THE INVENTION AND RELATED ART STATEMENT

This invention relates to a process and apparatus for the extraction and purification of DNA which can extract and purify DNA from a large number of test samples in a short period of time.

Conventionally, the boiling method (Holmes, D. S. and M. Quigley, 1981, Anal. Biochem. 114:193) and the alkaline lysis method (Birnboim, H. C. and J. Doly, 1979, Nucleic Acids Res. 7:1513) have been employed as methods for extracting and purifying plasmid DNA (extranuclear genes) from transformants obtained by transforming *Escherichia coli* and other bacteria. However, these methods involve the use of dangerous reagents such as phenol and chloroform, and hence require much labor and time.

Moreover, a process for the extraction and purification of plasmid DNA on the basis of cesium chloride density-gradient centrifugation is known as a method for the preparation of highly purified samples. Although this process is a typical one for achieving a high degree of purification, it requires such a long time that only about 10 samples can be treated at a time. Furthermore, various apparatus for performing conventional methods automatically have been developed. However, these apparatus generally have the disadvantage of being expensive and incapable of treating a sufficient number of samples, and are hence unsatisfactory for practical purposes.

Transformation is a basic technique used in genetic engineering and is now indispensable for research and development in the field of life science or biotechnology. Accordingly, it is desired to extract and purify extranuclear gene DNA from transformants obtained by this technique (in particular, ones obtained by transforming *Escherichia coli* and the like) in such a way that highly pure DNA can be obtained, with high safety, in a fully automatic manner and in a short period of time.

OBJECT AND SUMMARY OF THE INVENTION

The present invention has been made in view of the above-described problems, and an object thereof is to provide a process and apparatus for the extraction and purification of DNA wherein extranuclear gene DNA (plasmid DNA) replicated and amplified by transformants can be extracted and purified from overnight cultures in a fully automatic manner and at low cost.

The above object is accomplished by a process for the extraction and purification of DNA which comprises the steps of (a) moving a first tube rack having at least one first filter tube disposed therein and a second tube rack having at least one second filter tube disposed therein by means of transfer devices, so as to lay one of said tube racks on top of the other and define a vacuum chamber therebetween, (b) placing a transformant culture sample in said first filter tube and effecting the lysis of bacterial cells, the denaturation of unwanted proteins and chromosomal DNA, and optionally the hydrolysis of RNA, (c) filtering the sample through said first filter tube with the aid of a vacuum device to remove any impurities and transfer the filtrate to said second filter tube, and (d) effecting the adsorption, washing and elution of DNA in said second filter tube.

The above object is also accomplished by apparatus for the extraction and purification of DNA which comprises a first tube rack having disposed therein at least one first filter tube for the extraction and purification of DNA, a second tube rack having disposed therein at least one second filter tube for the extraction and purification of DNA, and a vacuum device for applying suction to the filters included in said first and second filter tubes.

DETAILED DESCRIPTION OF PREFERRED EMBODIMENTS

One embodiment of the DNA extraction and purification method and apparatus of the present invention will be described hereinbelow with reference to the accompanying drawings.

Figure 1:
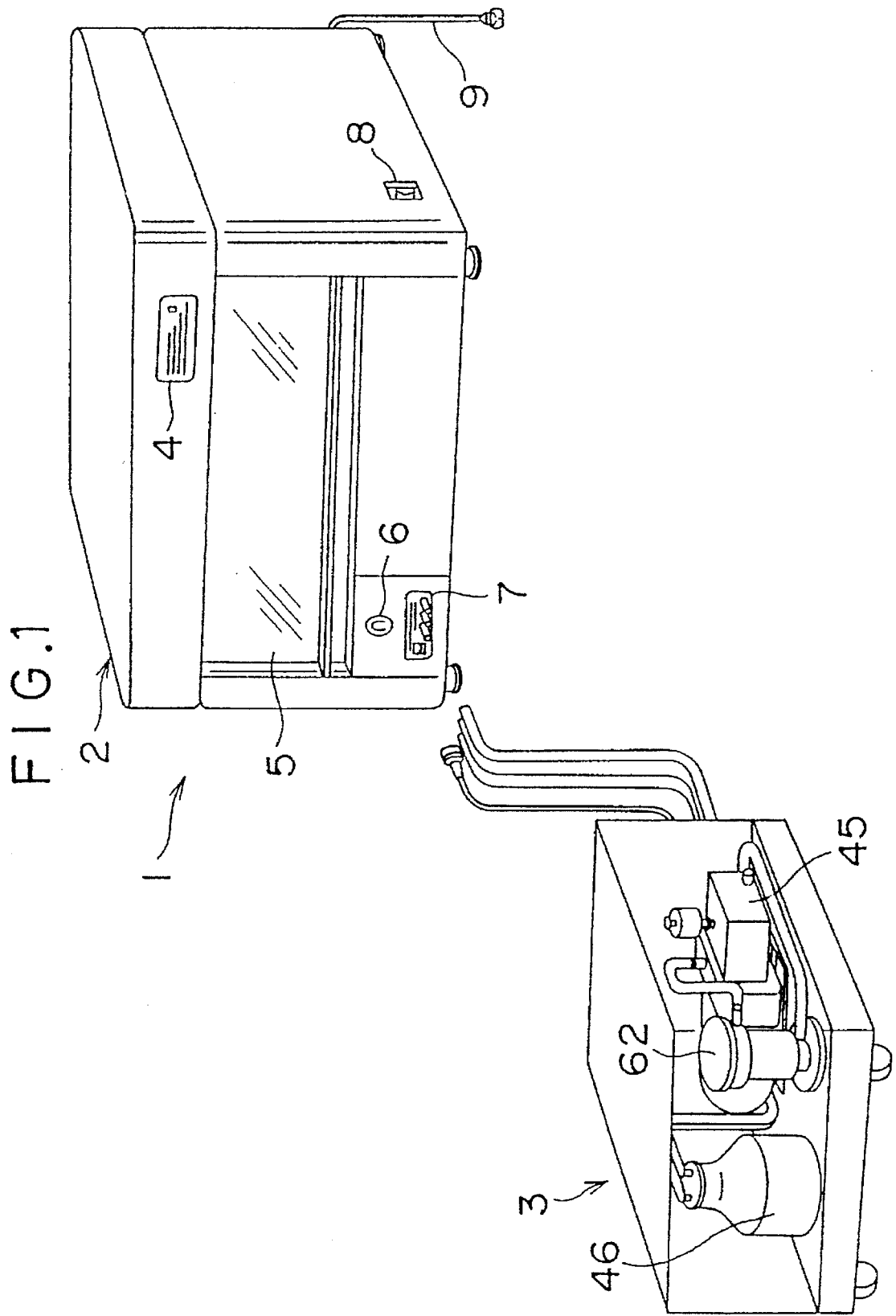
FIG. 1 is a general perspective view of DNA extraction and purification apparatus in accordance with one embodiment of the present invention.

FIG. 1 is a general view of DNA extraction and purification apparatus 1 in accordance with the present invention. This DNA extraction and purification apparatus 1 consists of a main body 2 and a wagon 3. Disposed on the front of main body 2 are a control panel 4, a door 5, a vacuum gage 6, and a connection port 7 for connecting piping and wiring from wagon 3. Moreover, a power switch 8 is disposed on one side of main body 2, and a power cord 9 on the back thereof. Furthermore, door 5 is provided with a switch (not shown) for detecting the opening or closing of the door.

Figure 2:
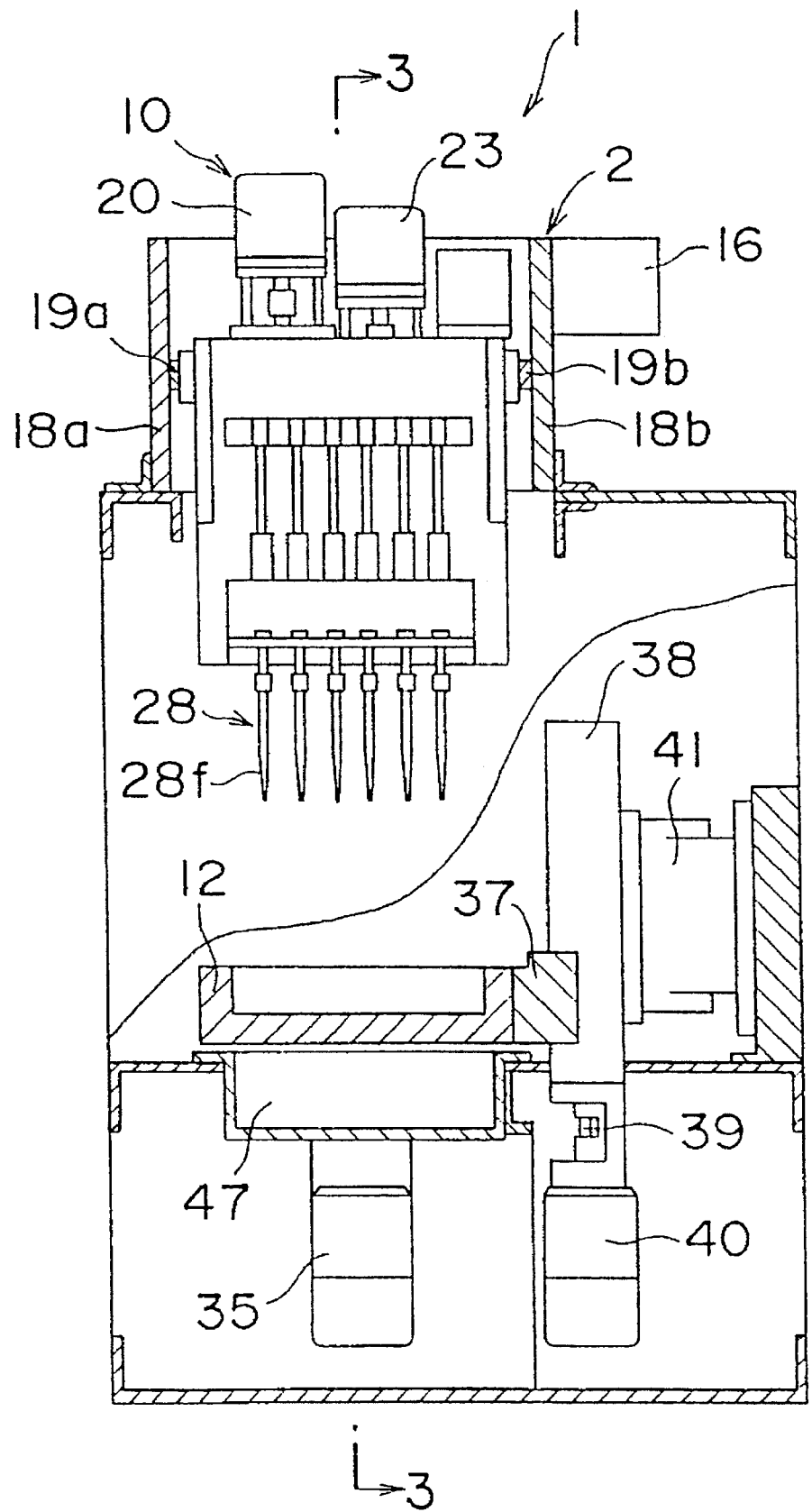
FIG. 2 is a side elevational view of the main body of the DNA extraction and purification apparatus of FIG. 1.
Figure 3:
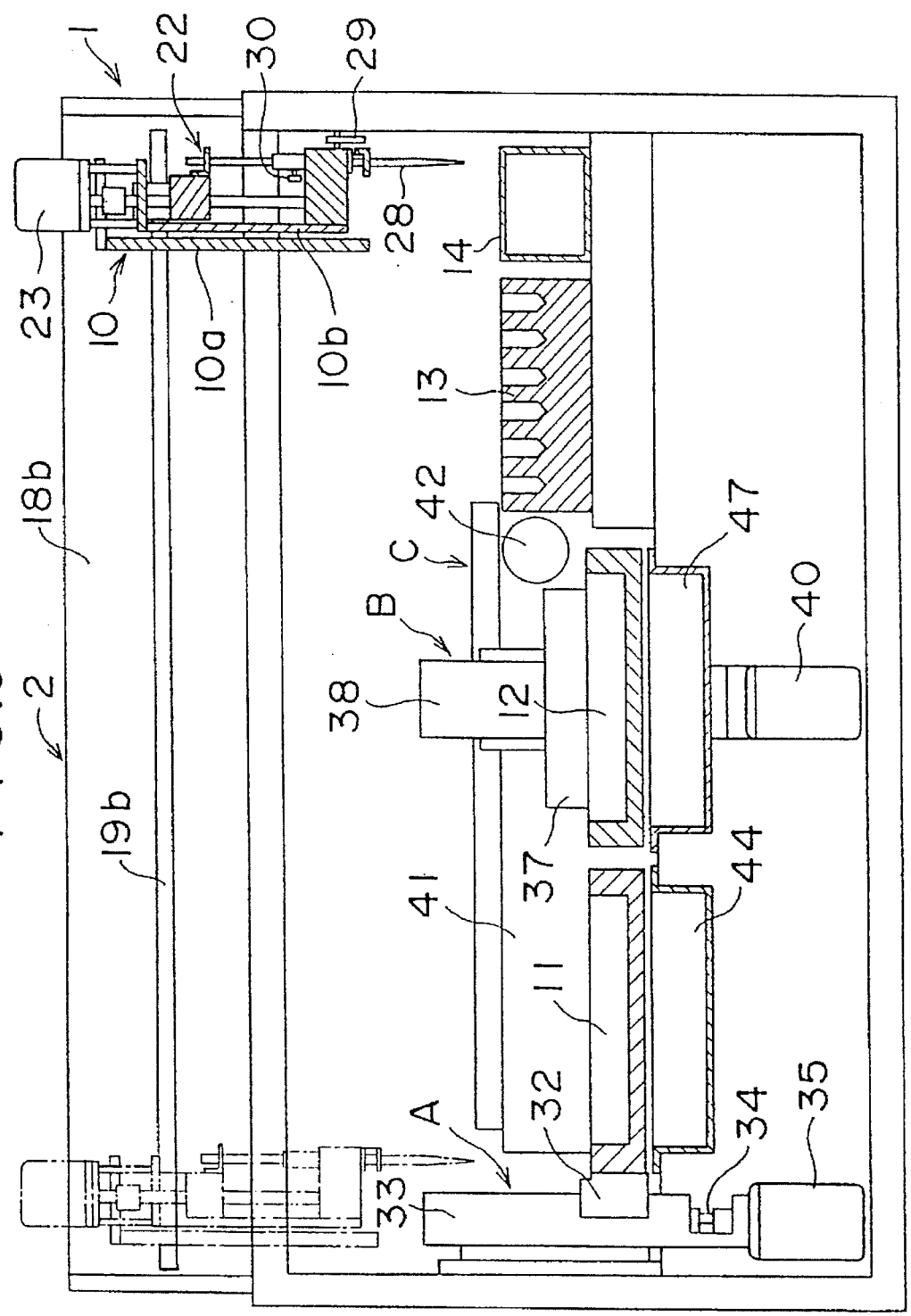
FIG. 3 is a longitudinal sectional view of the main body of the DNA extraction and purification apparatus of FIG. 1 as taken along line X—X in FIG. 2.
Figure 4:
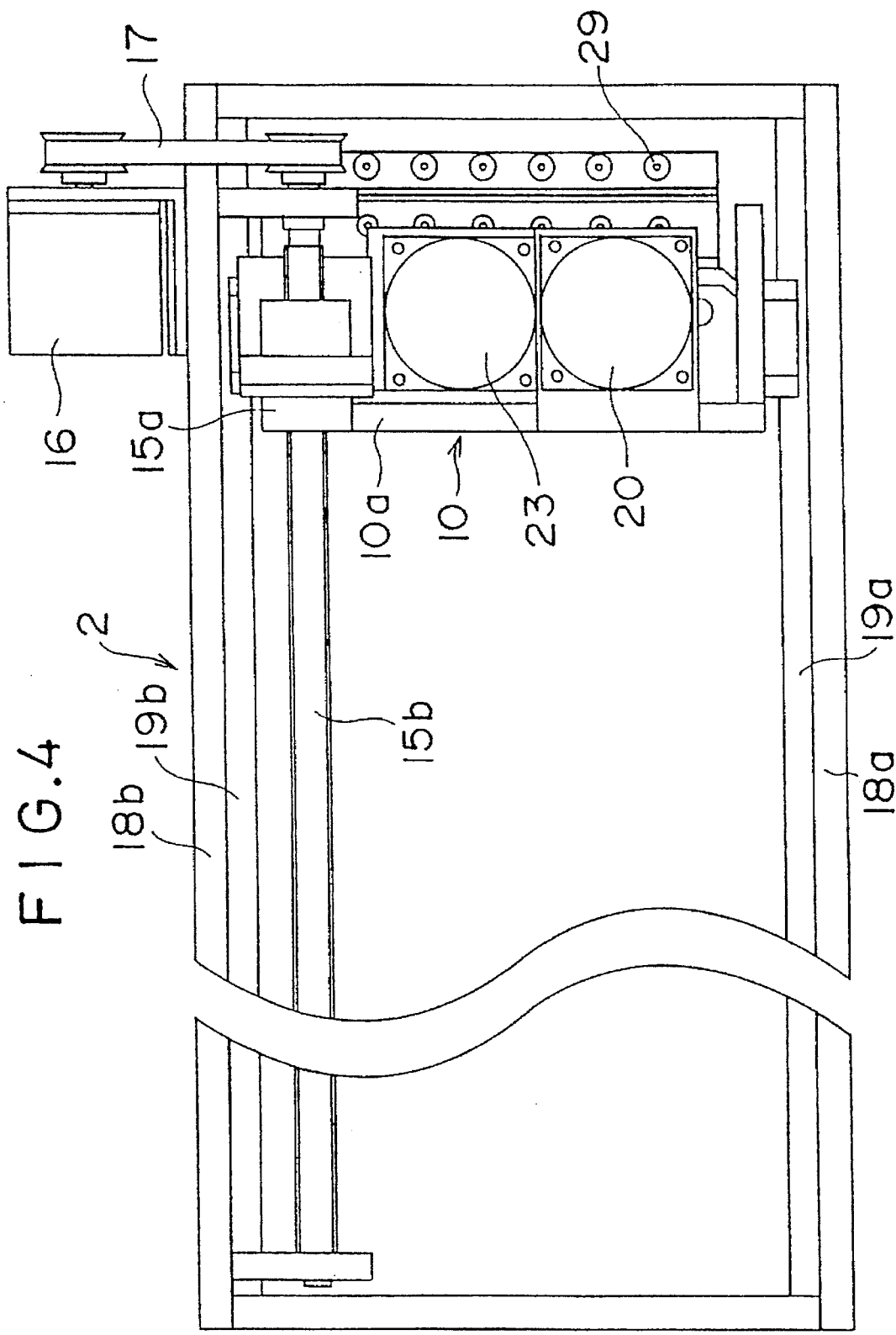
FIG. 4 is a plan view of the main body of the DNA extraction and purification apparatus of FIG. 1.

FIGS. 2 and 3 show the internal construction of main body 2. Main body 2 consists of a pipetting unit 10, a first tube rack 11, a second tube rack 12, a reservoir 13 and a tip stand 14. Pipetting unit 10 can be laterally moved within main body 2. The mechanism therefor is explained with reference to the plan view shown in FIG. 4. Pipetting unit 10 has a ball nut 15a attached to a main bracket 10a, and a ball screw 15b is engaged therewith. When a motor 16 is operated, ball screw 15b is rotated through the medium of a belt 17 and this causes pipetting unit 10 to move laterally along rails 19a and 19b fixed to guide plates 18a and 18b, respectively.

Figure 5:
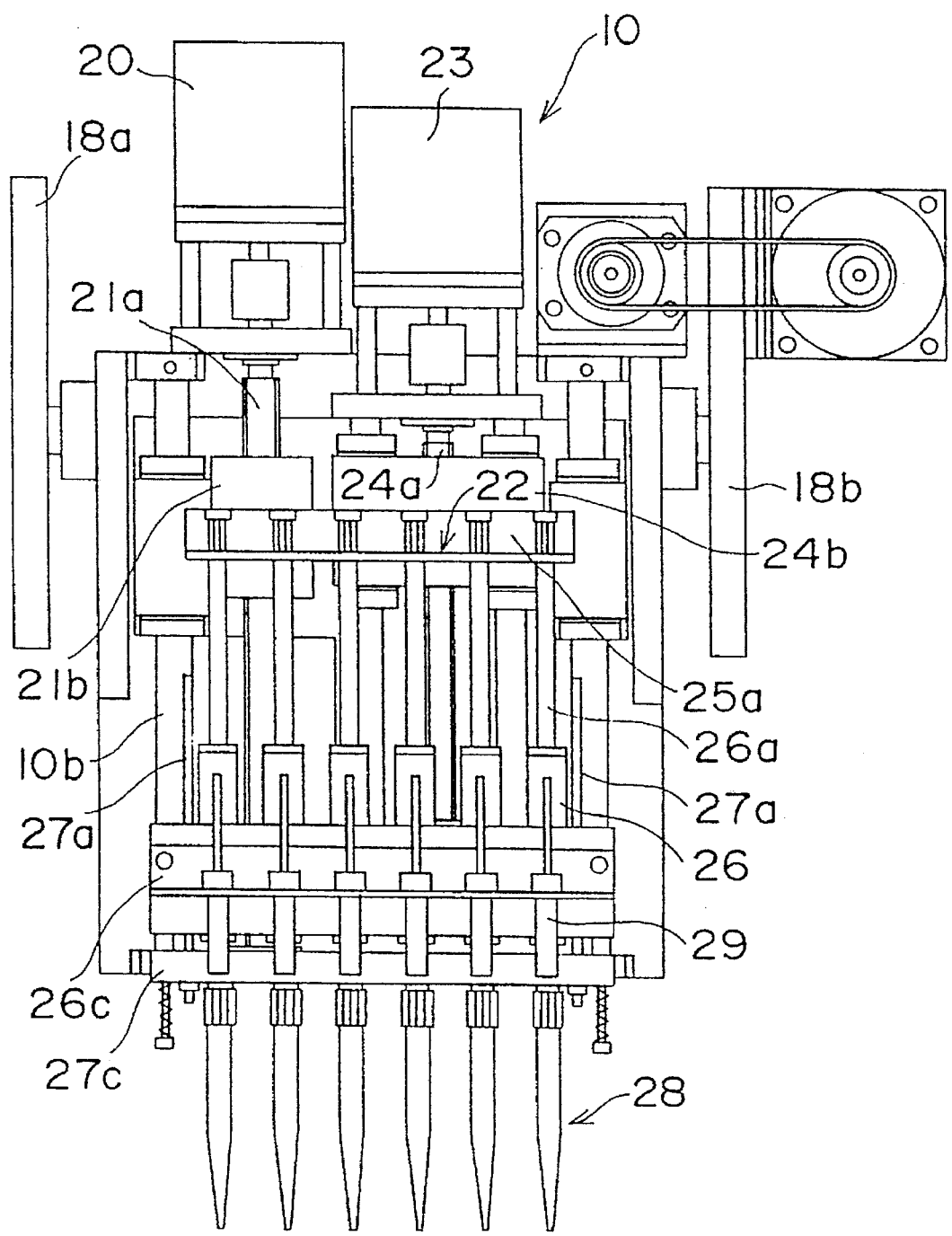
FIG. 5 is an enlarged side elevational view of a pipetting unit included in the DNA extraction and purification apparatus of FIG. 1.

Pipetting unit 10 has a height controlling motor 20 mounted on main bracket 10a. As shown in FIG. 5, a ball screw 21a is attached to the shaft of height controlling motor 20 and engaged with a ball nut 21b integrally fixed to a sub-bracket 10b. When height controlling motor 20 is operated, a pipetting section 22 attached to sub-bracket 10b as shown in FIG. 3 is lowered.

As shown in FIG. 5, pipetting unit 10 has a ball screw 24a attached to the shaft of a pipetting motor 23, and this ball screw 24a is engaged with a ball nut 24b integrally fixed to a piston mounting stay 25a. When pipetting motor 23 is operated, stay 25a is moved upward or downward, causing a corresponding vertical motion of the piston shafts 26a of six cylinders 26. These cylinders 26 serve to suck up and discharge reagents for the extraction and purification of DNA. When stay 25a is further lowered, the underside of stay 25a strikes against the top of rods 27a. Since these rods 27a are fixed to a detaching plate 27c for piper tips 28, detaching plate 27c forces down and thereby detaches pipet tips 28.

Six tube detection sensors 29 for judging the presence or absence of tubes are mounted on one side of a cylinder block 26c supporting cylinders 26. These tube detection sensors 29 use reflection type photoelectric devices. Moreover, one of cylinders 26 is fitted with a liquid level sensor 30 as shown in FIG. 3. This liquid level sensor 30 measures the level of the liquid surface by detecting a sudden change in air pressure during discharging operation (see Japanese Patent Laid-Open No. 232124/'93).

As shown in FIG. 3, a first transfer device A functions to move first tube rack 11 vertically. tube rack 11 being removably attached to a gripping member 32. Gripping member 32 is slidably fitted over a guide plate 33 and engaged with a ball screw 34 extending parallel to guide plate 33. When a driving motor 35 attached to the bottom of guide plate 33 is operated, gripping member 32, together with tube rack 11, is vertically moved along guide plate 33.

A second transfer device B functions to move second tube rack 12 vertically, tube rack 12 being removably attached to a gripping member 37. Gripping member 37 is slidably fitted over a guide plate 38 and engaged with a ball screw 39 (see FIG. 2) extending parallel to guide plate 38. When a driving motor 40 attached to the bottom of guide plate 38 is operated, gripping member 37 is vertically moved along guide plate 38. A third transfer device C functions to move second tube rack 12 horizontally. guide plate 38 being slidably fitted over a slide plate 41. When a driving motor 42 disposed at an end of slide plate 41 is operated, guide plate 38 is horizontally moved along slide plate 41 under the action of the force transmitted by a belt (not shown).

Figure 6:
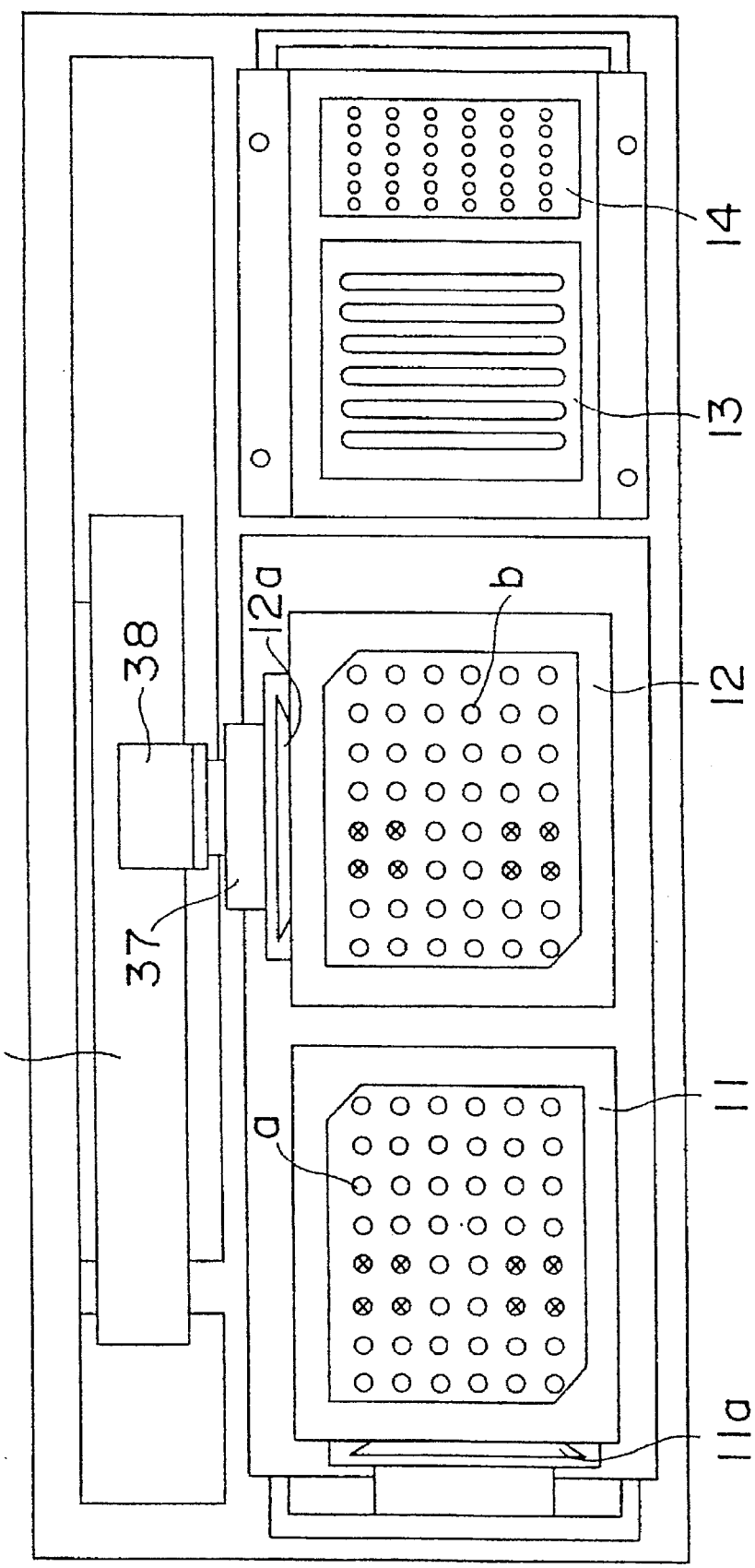
FIG. 6 is a plan view of the lower part of the main body of the DNA extraction and purification apparatus of FIG. 1.

As shown in FIG. 6, first tube rack 11 and second tube rack 12 have the same appearance and shape except for the position of a handle 11a or 12a to be attached to the above-described gripping member 32 or 37, respectively.

Figure 7:
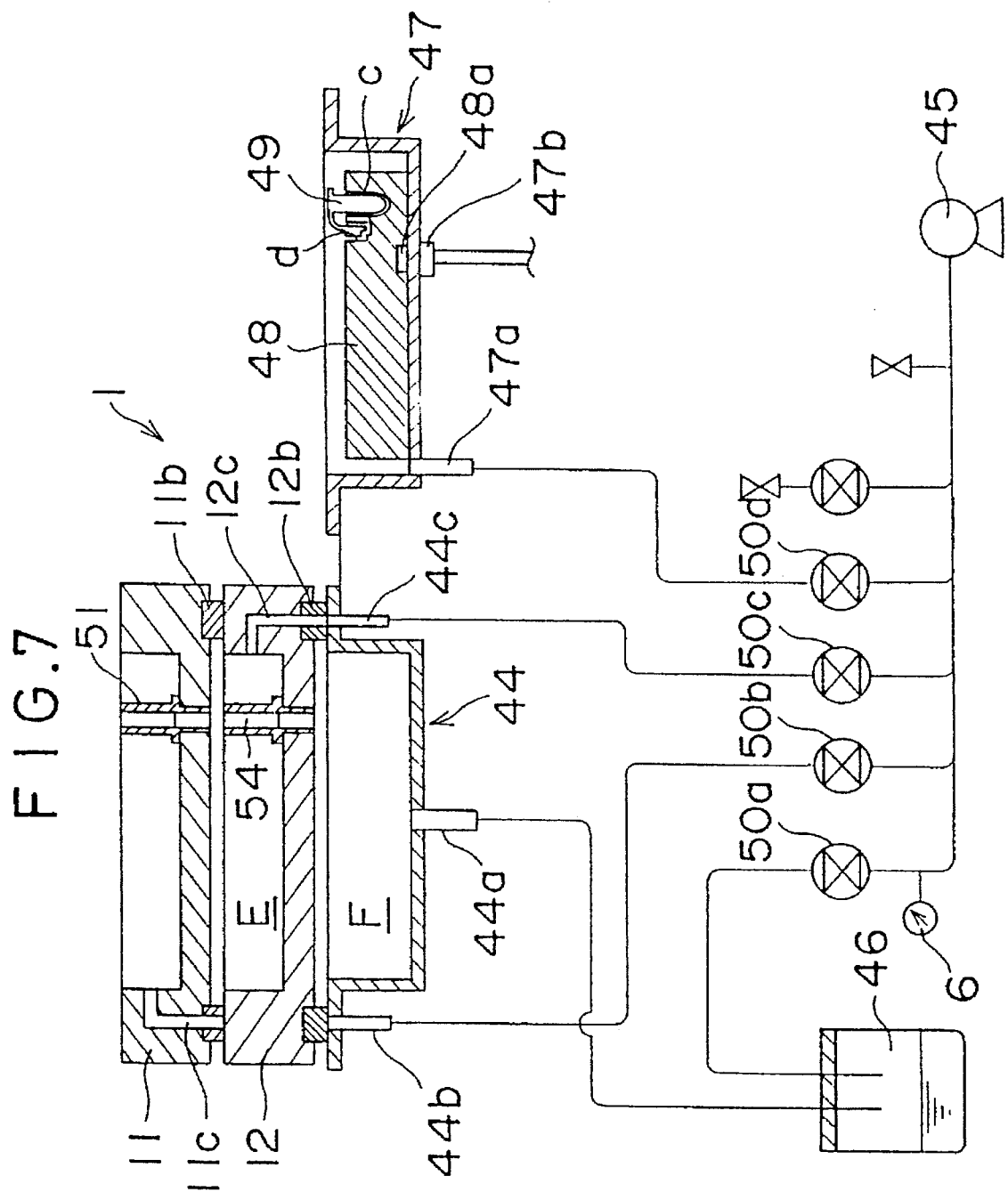
FIG. 7 is a schematic sectional view of a vacuum conveyor section included in the DNA extraction and purification apparatus of FIG. 1.
Figure 8:
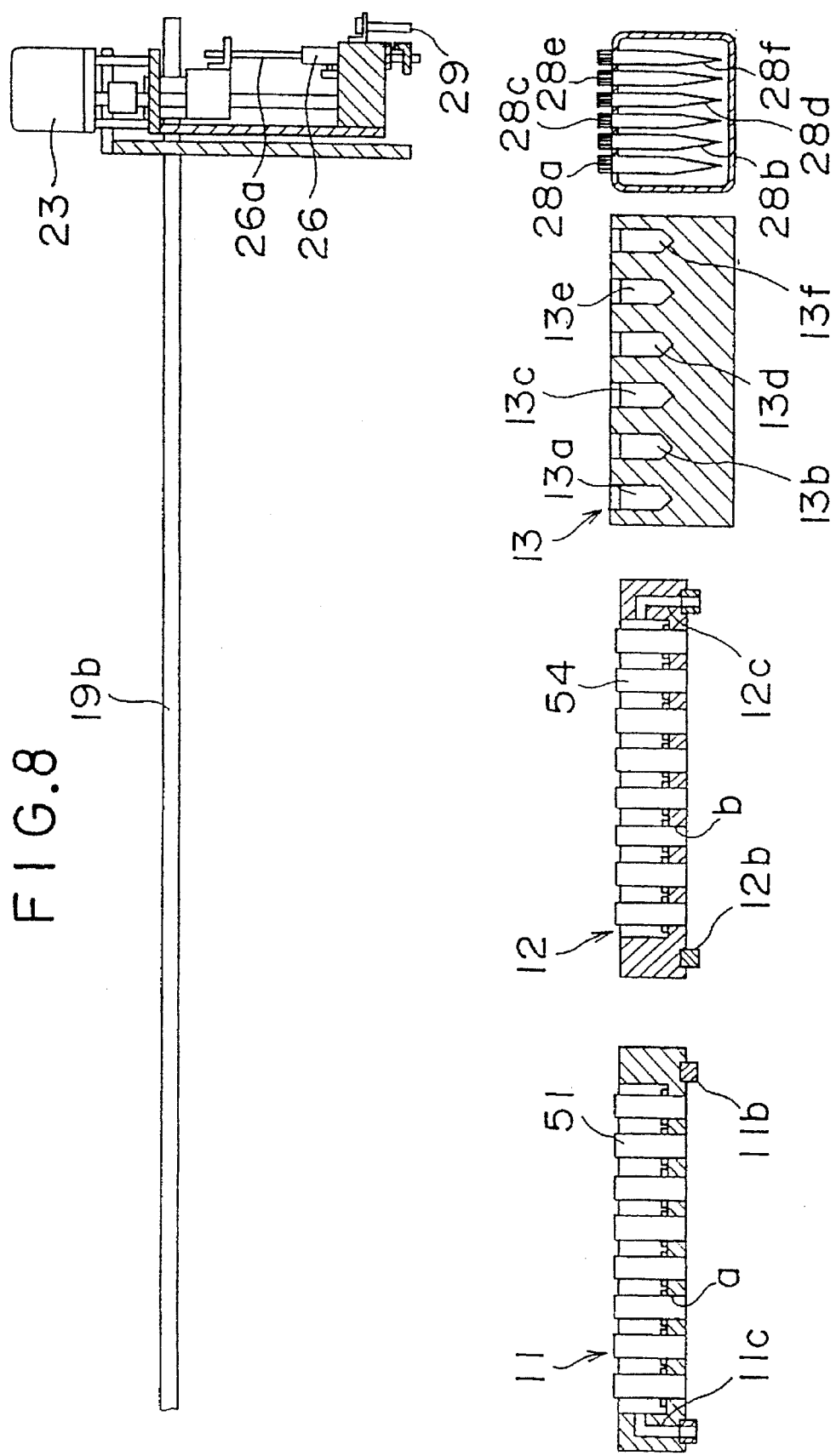
FIG. 8 is a schematic sectional view of the lower part of the main body of the DNA extraction and purification apparatus of FIG. 1.

Therefore, holes a and b bored through the bottom walls thereof are equal in number and position. As a result, when they are laid one on top of the other, holes a align vertically with holes b. As shown in FIGS. 7 and 8, tube racks 11 and 12 are fitted with rubber gaskets 11b and 12b, respectively, at the bottom. Moreover, tube racks 11 and 12 are provided with passages 11c and 12c, respectively. These passages 11c and 12c extend through rubber gaskets 11b and 12b and through the bottom wall and inner side wall of tube racks 11 and 12, respectively.

As shown in FIG. 3, a waste liquid vat 44 is disposed below first tube rack 11. As shown in FIG. 7, the bottom of waste liquid vat 44 is provided with a suction port 44a which is connected to an electromagnetic valve 50a via a waste water trap 46 in wagon 3. Moreover, the lateral edges of waste liquid vat 44 are provided with suction ports 44b and 44c which are connected to electromagnetic valves 50b and 50c, respectively. These electromagnetic valves 50a to 50c are connected to a vacuum pump 45 disposed in wagon 3.

As shown in FIG. 7, DNA extraction and purification apparatus 1 also includes a recovery vat 47 disposed adjacent to waste liquid vat 44. Disposed in this recovery vat 47 is a recovery rack 48 having holes c made at the same positions as holes b of second tube rack 12. Recovery tubes 49 are held in these holes c and caps for recovery tubes 49 are held in holes d made near to holes c. The positions at which these recovery tubes 49 are disposed correspond to the positions at which filter tubes 54 are disposed in tube rack 12 (i.e., the positions of holes b occupied by filter tubes 54), and holes c have substantially the same shape as recovery tubes 49. The bottom of recovery vat 47 is provided with a suction port 47a which is connected to an electromagnetic valve 50d. This electromagnetic valve 50 dis connected to vacuum pump 45. Moreover, the bottom of recovery vat 47 is fitted with a magnetic sensor 47b which is electrically connected to a sequencer 60 (see FIG. 12), and a magnet 48a is fixed to the bottom of recovery rack 48. For this purpose, one or more magnetic sensors and magnets may be used at one or more corresponding positions so that they align with each other when recovery rack 48 is disposed in the right place. Although a large number of filter tubes 51, filter tubes 54 and recovery vat 47 are disposed in tube rack 11, tube rack 12 and recovery rack 49, only one each of tubes 49, 51 and 54 is shown in FIG. 7 for purposes of simplification.

Figure 9:
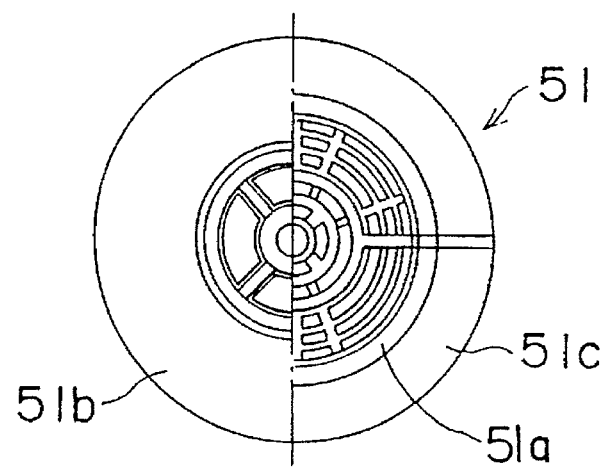
FIG. 9A is a plan view of a filter tube as seen from above and below.
FIG. 9B is a partially sectional view of the filter tube.
Figure 9:
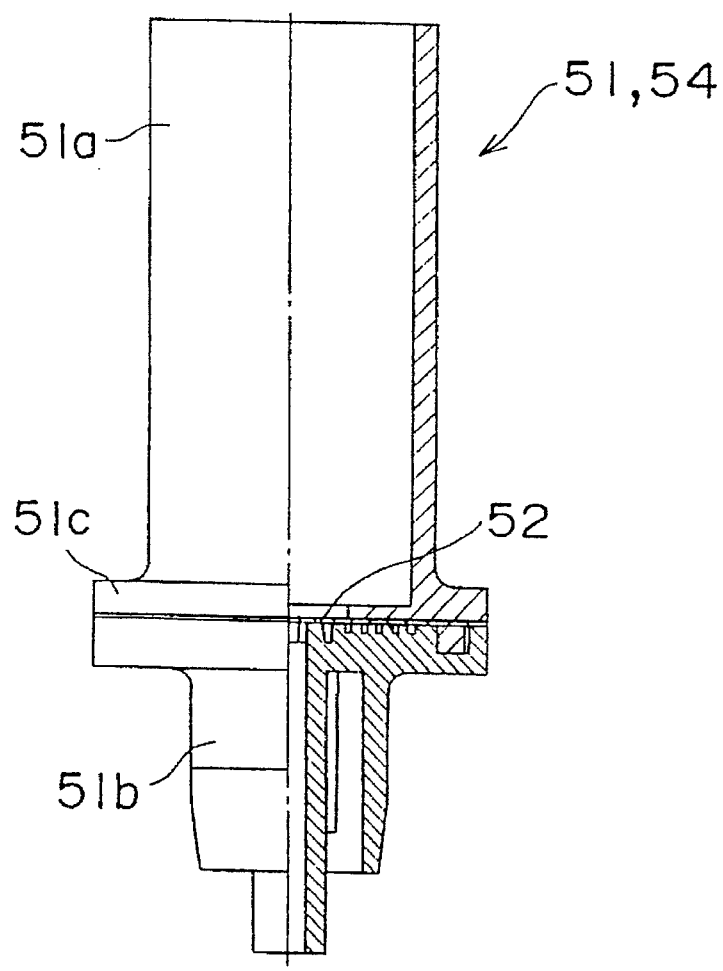

As shown in FIG. 6, a large number of holes a are bored through the bottom wall of first tube rack 11 as described above, and first filter tubes 51 are inserted into these holes as shown in FIG. 8. As shown in FIG. 9, each filter tube 51 consists of a top piece 51a and a bottom piece 51b, and the lower part of bottom piece 51b is inserted into a hole a of tube rack 11. Filter tube 51 is usually in a cylindrical shape and preferably has a diameter of 10 to 20 mm and a length of 30 to 50 mm.

Figure 10:
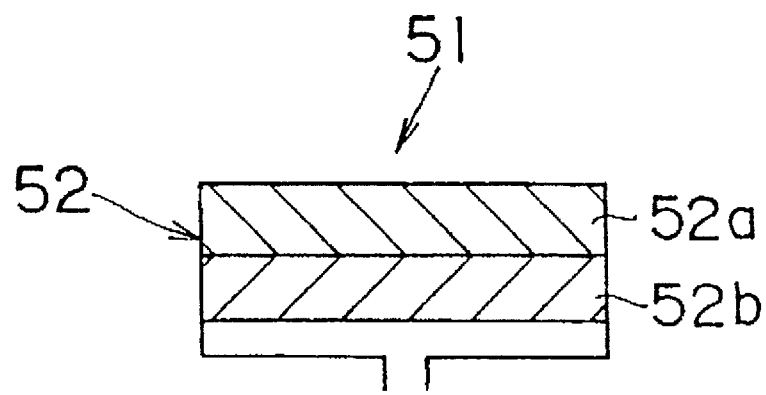
FIG. 10 is an enlarged sectional view of a filter assembly included in a first filter tube.

A filter assembly 52 is included in the flange 51c of each first filter tube 51, and a sectional view of this filter assembly 52 is shown in FIG. 10. A trap filter 52a is a layer serving primarily to capture the transformed cells of *Escherichia coli* or the like and effect the lysis thereof. Preferably, this trap filter 52a comprises a glass fiber filter, polyethylene resin filter, nonwoven fabric filter or the like and has the property of sterically capturing the transformed cells of *Escherichia coli* or the like.

A membrane filter 52b is a layer serving primarily to filter off unwanted materials such as coagulated proteins and chromosomal DNA. Preferably, this membrane filter 52b consists of a material such as cellulose acetate or polyvinylidene fluoride and has such properties as biological inertness and low protein adsorptivity. The holes a of tube rack 11 which are not fitted with filter tubes 51 are airtightly closed with black blank plugs.

Figure 11:
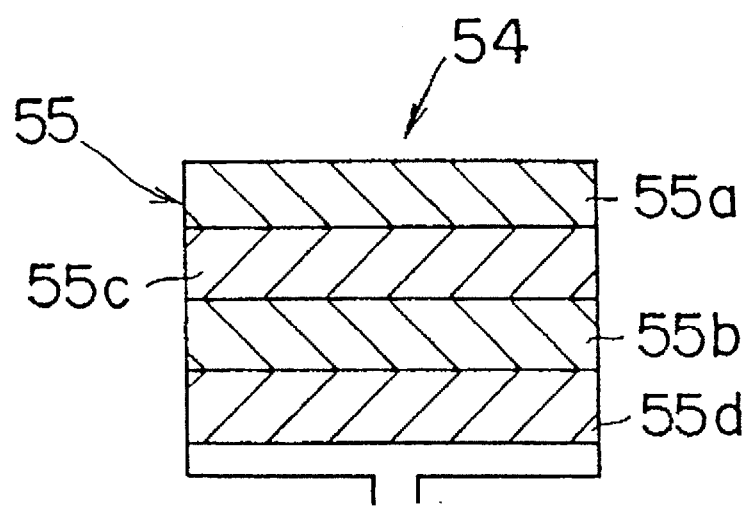
FIG. 11 is an enlarged sectional view of a filter assembly included in a second filter tube.

FIG. 11 illustrates a filter assembly 55 included in each of second filter tubes 54 supported in the holes of second tube rack 12. Second filter tubes 54 have the same construction as first filter tubes 51, except for filter assembly 55. Glass fiber filters 55a and 55b are layers serving primarily to aid in the adsorption of plasmids. Preferably, they consist of a material such as fine borosilicate glass fibers and have the property of being inert to biochemical fluids.

A glass powder layer 55c serves primarily to adsorb DNA. Preferably, it consists of a material such as silica matrix and has a sedimentation velocity of not greater than 0.25 cm/min in water. The function and material of a membrane filter 55d are the same as those of membrane filter 52b for use in first filter tubes 51. The holes b of tube rack 12 which are not fitted with filter tubes 52 are airtightly closed with black blank plugs.

The compartments 13a to 13f of reservoir 13 shown in FIG. 8 serve to hold reagents for the extraction and purification of DNA, as well as a washing fluid. The details thereof will be described later.

Figure 12:
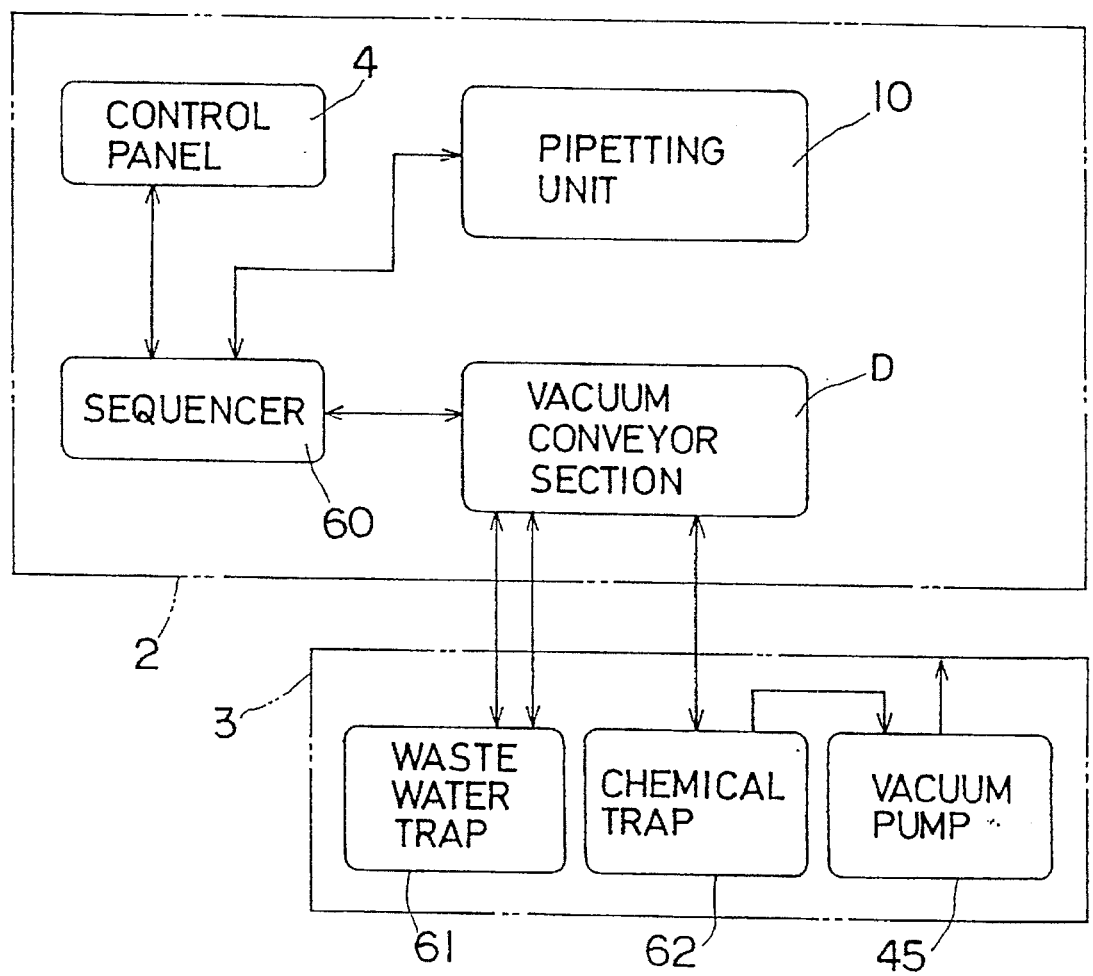
FIG. 12 is a diagrammatic view illustrating the system configuration of the DNA extraction and purification apparatus of the present invention.

FIG. 12 is a diagrammatic view illustrating the system configuration of the DNA extraction and purification apparatus. A sequencer 60, which constitutes a control section, is electrically connected to a control panel 4, a pipetting unit 10, and a vacuum conveyor section D including tube racks 11 and 12, etc. Vacuum conveyor section D is connected to a waste water trap 61 installed in a wagon 3 by means of piping. Moreover, Vacuum conveyor section D is connected to a vacuum pump 45 via a chemical trap 62 by means of piping.

Having described the construction of apparatus for the extraction and purification of DNA in accordance with one embodiment of the present invention, the operation thereof will now be described hereinbelow.

Prior to starting the operation of DNA extraction and purification apparatus 1 illustrated in FIG. 1, door 5 is opened and first filter tubes 51, second filter tubes 54, recovery tubes 49, reagents and pipet tips 28 are set in place. As samples, transformant cultures have previously been placed in filter tubes 51 shown FIG. 8. For this purpose, there may be used transformants obtained by transforming a host microorganism [i.e., E. coli HB101 (ATCC 33694) ] according to the method of Hanahan (Hanahan, D., 1983, J. Mol. Biol., 166, 577).

Figure 13:
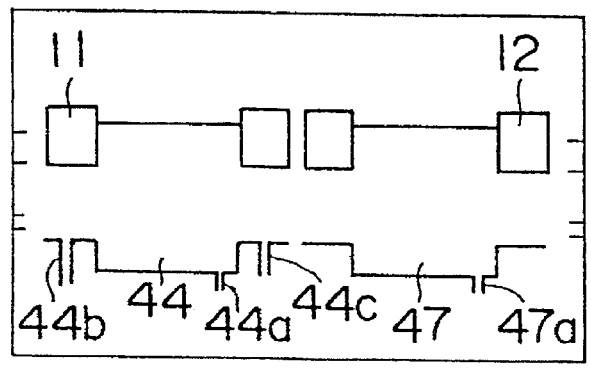
FIGS. 13A to 13C are schematic views showing several modes of arrangement of first and second tube racks.
Figure 13:
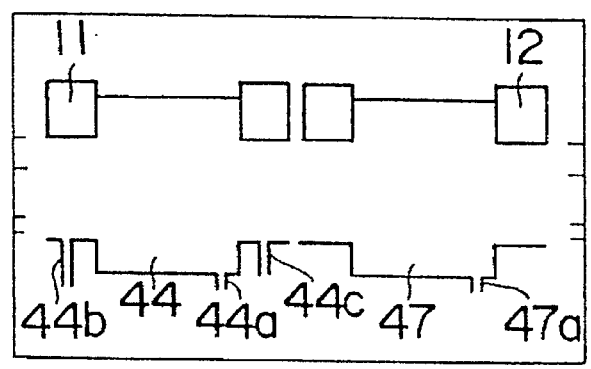
Figure 13:
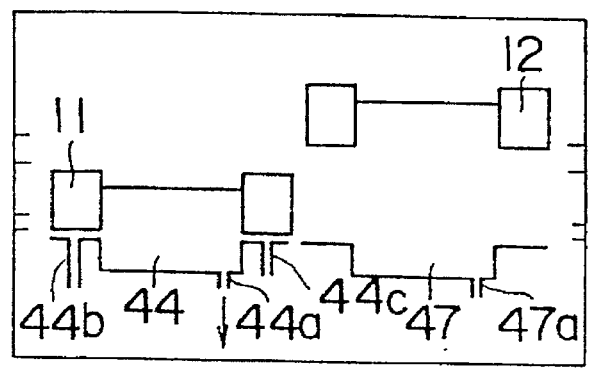

First of all, DNA extraction and purification apparatus 1 is turned on by means of power switch 8. If door 5 is properly closed, a detection switch (not shown) detects the closed state of door 5 and locks it, for example, with the aid of an interlock solenoid or the like. Then, pipetting unit 10, first tube rack 11 and second tube rack 12 are placed in their initial positions shown in FIG. 8. The arrangement of tube racks 11 and 12 in this stage is schematically shown in FIG. 13A. As shown in the drawings, tube racks 11 and 12 can be vertically moved to any one of four levels 0-3 (numbered 0, 1, 2 and 3 from the lowest mark upward) by operating the above-described transfer devices A and B, and they are positioned at level 2 in the initial stage. After the initial settings of DNA extraction and purification apparatus 1 have been completed, door 5 is unlocked.

After the door 5 of DNA extraction and purification apparatus 1 is opened, filter tubes 51 and 54, recovery tubes 49 and pipet tips 28 are set in place as shown in FIG. 8. Moreover, specified reagents are poured into the compartments 13a–13f of reservoir 13. Thereafter, door 5 is closed and a start key disposed on control panel 4 is pressed.

When the start key is pressed, DNA extraction and purification apparatus 1 performs actions for confirming that filter tubes and reagents are correctly set. That is, in the action for confirming the presence of filter tubes, both tube racks 11 and 12 are positioned at level 3 as shown in FIG. 13B. Then, pipetting unit 10 shown in FIG. 8 is horizontally moved to the left and back, during which time the presence of filter tubes 51 and 54 is confirmed by tube detection sensors 29 mounted on pipetting unit 10.

More specifically, when filter tubes 51 and 54 are inserted, for example, in the holes of tube racks 11 and 12 which are marked with a cross (x) as shown in FIG. 6, this action is performed to confirm that the setting patterns of filter tubes 51 and 54 in tube racks 11 and 12 are the same and that these setting patterns conform to the rules of the apparatus. In this case, since other holes of tube racks 11 and 12 than those marked with a cross (x) are closed with black blank plugs, tube detection sensors 29 detect a difference in light reflectance between filter tubes 51 or 54 and blank plugs, and thereby judge the setting patterns of filter tubes 51 and 54. If the setting patterns are not correct, an error occurs and the apparatus comes to a pause. If the setting patterns are correct, the apparatus proceeds to the action for confirming the quantities of reagents.

In the action for confirming the quantities of reagents, height controlling motor 20 is operated to lower sub-bracket 10b and attach thereto a first row of pipet tips 28a in tip stand 14. Then, by moving pipetting unit 10, pipet tips 28a are inserted into the reagent within the first compartment 13a of reservoir 13 and the quantity of the reagent is measured by means of liquid level sensor 30. Thereafter, pipetting unit 10 is moved back to above tip stand 14 and pipet tips 28a are detached and returned to their places. Next, using a second row of pipet tips 28b, the quantity of the reagent within compartment 13b is measured in substantially the same manner. Similarly, the quantities of the reagents within compartments 13c to 13f are measured successively. Thus, the quantities of the reagents are checked to see if they are sufficient for the number of filter tubes 51 and 54 used. Pipet tips 28a to 28f are used in such an order as to correspond to compartments 13a to 13f. When the quantities of the reagents are above their specified levels and the setting patterns are correct, DNA extraction and purification apparatus 1 proceeds to the step of effecting the lysis of bacterial cells, the denaturation of unwanted proteins and chromosomal DNA, and optionally the hydrolysis of unwanted RNA.

In the step of effecting the lysis of bacterial cells, the denaturation of unwanted proteins and chromosomal DNA, and optionally the hydrolysis of unwanted RNA, tube rack 11 is positioned at level 0, i.e., in contact with the top of waste liquid vat 44, as shown in FIG. 13C. Since the bottom of tube rack 11 is fitted with rubber gasket 11b, airtight contact is established therebetween. Then, by operating vacuum pump 45 for 2 minutes, air is drawn out through suction port 44a and this causes the liquid, except bacterial cells, to be filtered and removed from filter tubes 51.

Figure 14A:
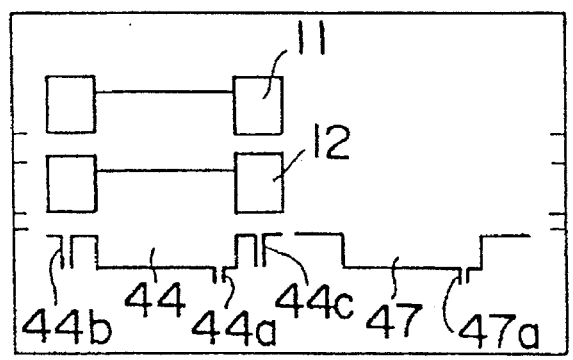
FIGS. 14A to 14C are schematic views showing several modes of arrangement of the first and second tube racks.

Next, tube racks 11 and 12 are transferred from their respective positions shown in FIG. 13C to those shown in FIG. 14A. That is, under the automatic control of DNA extraction and purification apparatus 1, tube rack 11 is raised to level 3 (i.e., the position for reagent addition) while tube rack 12 is lowered to level 1 and then moved to the left. Then, pipetting unit 10 sucks a bacteriolytic reagent from compartment 13a into pipet tips 28a and adds 200–400 µl of the bacteriolytic reagent to the trap filter 52a of each filter tube 51. Thereafter, filter tubes 51 are allowed to stand at room temperature for 10 minutes. In this step, transformed bacterial cells are lysed to release extranuclear genes (plasmid DNA) from the cells. In this step, the bacteriolytic reagent may digest unwanted RNA at the same time. For this purpose, there is used a bacteriolytic reagent containing lysozyme as a bacteriolytic enzyme and ribonuclease A as an RNase.

Next, the step of removing impurities by filtration through first filter tubes 51 is carried out. In this step, by moving pipetting unit 10, a reagent for the complete solubilization of samples is sucked from compartment 13b into pipet tips 28b and added to the trap filter 52a of each filter tube 51. Then, the samples are completely solubilized by allowing filter tubes 51 at room temperature for 5 minutes. In order to solubilize the samples completely, 400 µl of a reagent comprising a 0.2N sodium hydroxide solution containing 1% sodium lauryl sulfate is added to each filter tube 51.

Subsequently, by moving pipetting unit 10, 3M potassium acetate (pH 4.8) is sucked from compartment 13c into pipet tips 28c and 300 µl of it is added to the trap filter 52a of each filter tube 51. Then, filter tubes 51 are allowed to stand at room temperature for 5 minutes, so that the basic solution is neutralized and, at the same time, cellular proteins and chromosomal DNA are coagulated.

Figure 14B:
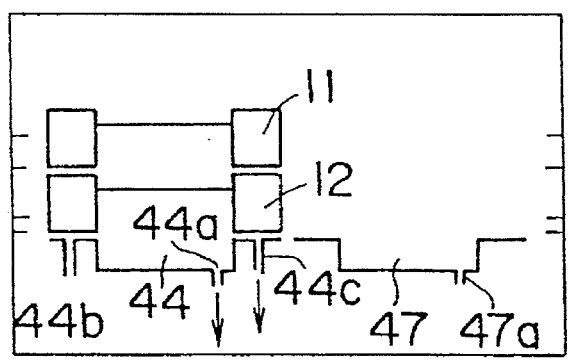

Thereafter, the step of effecting the adsorption, washing and elution of DNA in second cartridges is carried out. In this step, by moving pipetting unit 10, a DNA adsorption reagent comprising 8M sodium iodide (NaI) or 10M sodium thiocyanate (NaSCN) is sucked from compartment 13d into pipet tips 28d and added to filter tubes 51. Then, tube racks 11 and 12 are moved to the respective positions shown in FIG. 14B. That is, tube rack 12 is lowered to level 0 and tube rack 11 is likewise lowered to level 2.

In this state, as shown in FIG. 7, tube rack 11 is laid on top of tube rack 12 to define a vacuum chamber E, and tube rack 12 is laid on top of waste liquid vat 44 to define a vacuum chamber F. The bottom of tube rack 11 is fitted with a rubber gasket 11b, so that airtight contact is established between tube racks 11 and 12. Likewise, the bottom of tube rack 12 is fitted with a rubber gasket 12b, so that airtight contact is established between tube rack 12 and waste liquid vat 44.

Air is drawn out through suction ports 44a and 44c by operating vacuum pump 45 for 10 minutes. As a result, suction is applied to the tube filters 51 of tube rack 11 through suction port 44c and passage 12c formed in the side wall of tube rack 12. Thus, the plasmid extracts are transferred from first filter tubes 51 to second filter tubes 54.

In this step, plasmid DNA is adsorbed to the glass powder layer 55c of each second filter tube 54. In order to transfer the samples from first filter tubes 51 to second filter tubes 54 by suction, it is only necessary to evacuate space F. However, if there is a pressure difference between vacuum chambers E and F at the start of evacuation or at the time of vacuum breaking, the samples transferred to second filter tubes 54 may escape to waste liquid vat 44. For this reason, passage 12c is formed in tube rack 12 so that vacuum chambers E and F may be evacuated to the same reduced pressure.

Figure 14C:
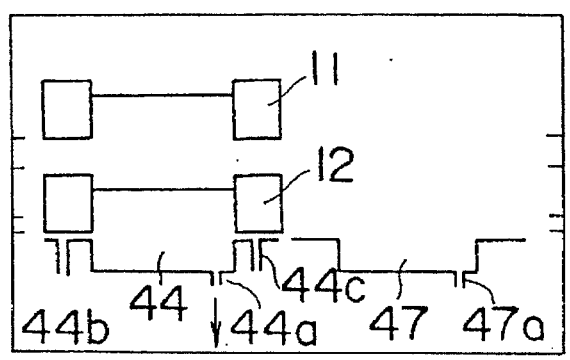

Then, as shown in FIG. 14C, only tube rack 11 is raised to level 3 and electromagnetic valve 50a connected to suction port 44a is opened to apply suction to the filter tubes 54 of tube rack 12 by operating the vacuum pump for 2 minutes. Thus, the sodium iodide solution within filter tubes 54 is removed by suction filtration.

Figure 15:
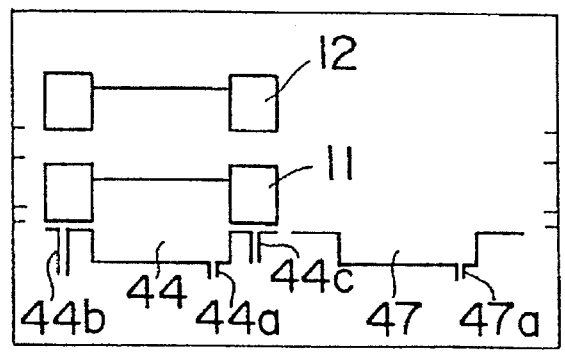
FIGS. 15A to 15C are schematic views showing several modes of arrangement of the first and second tube racks.
Figure 15:
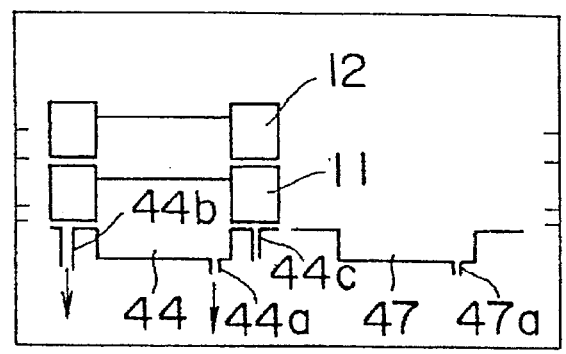
Figure 15:
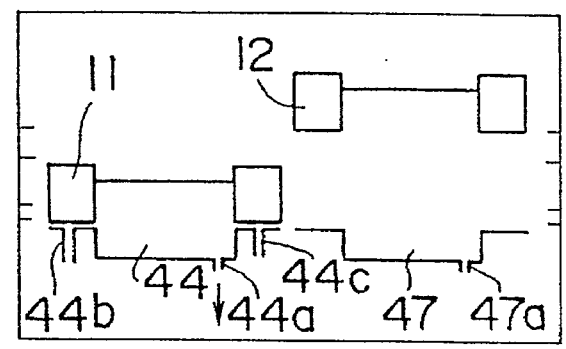

In the succeeding washing step, as shown in FIG. 15A, the arrangement of tube racks 11 and 12 is the reverse of the arrangement shown in FIG. 14C. That is, starting from the state of FIG. 14C, tube rack 12 is moved to the right and tube rack 11 is lowered to level 0. Subsequently, tube rack 12 is raised to level 3 and move to the left. Then, using pipet tips 28e of pipetting unit 10, 1,000 µl of a washing buffer solution comprising 10 mM tris-hydrochloric acid (pH 8.0), 1 mM EDTA and 0.2M NaCl in 50% ethanol is added to each filter tube 54.

Subsequently, as shown in FIG. 15B, tube rack 11 is lowered to level 0 and tube rack 12 is lowered to level 2. By opening electromagnetic valves 50a and 50b, suction is applied through suction ports 44a and 44b for 15 minutes by means of the vacuum pump, so that the washing fluid is withdrawn from filter tubes 54 into filter tubes 51. Since the arrangement of tube racks 11 and 12 in this step is the reverse of the arrangement shown in FIG. 7, the passage 11c of tube rack 11 communicates with suction port 44b, so that the washing fluid within filter tubes 54 is sucked out. Thereafter, a second washing step is carried out. This washing step is substantially the same as the above-described one, except that the washing buffer solution is used in a volume of 500 µl. Subsequently, as shown in FIG. 15C, tube rack 12 is raised to level 3 and moved to the right. Then, using pipet tips 28f of pipetting unit 10, 50–200 µl of an eluting buffer solution comprising 10 mM tris-hydrochloric acid (pH 8.0) and 1 mM EDTA in distilled water is added to each filter tube 54.

Figure 16:
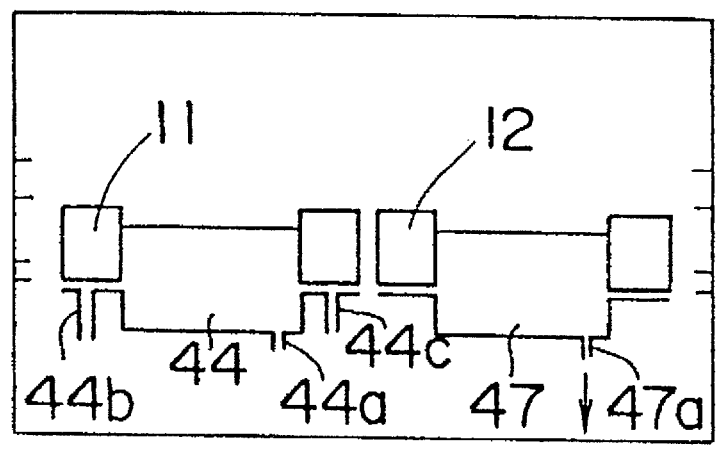
FIG. 16 is a schematic view showing a mode of arrangement of the first and second tube racks.

By opening electromagnetic valve 50a, the waste liquid within filter tubes 54 is sucked out by means of vacuum pump 45. Then, as shown in FIG. 16, tube rack 12 is lowered to level 0. By opening electromagnetic valve 50d, plasmid DNA is withdrawn from filter tubes 54 and collected in recovery tubes 49 disposed in recovery vat 47. If recovery rack 48 is not disposed or not positioned in the right place, misalignment of magnetic sensor 47b and magnet 48a is detected and an alarm is given at the start of the operation. However, if it has been forgotten to dispose recovery tubes 49 in recovery rack 48, the operation is continued without a break. In such a case, plasmid DNA is collected in the holes c of recovery rack 48 and, therefore, may be transferred to suitable containers afterwards.

Thus, according to the above-described embodiment of the present invention, plasmid DNA required for use in genetic recombination techniques can be extracted and purified in a fully automatic manner and in a short period of time (about 2 hours). Moreover, since the extraction and purification of DNA is carried out by suction through filters, highly pure plasmid DNA can be obtained at low cost.

While the present invention has been described in connection with one preferred embodiment thereof, it is to be understood that the present invention is not limited thereto but various modifications may be made on the basis of the technical idea thereof.

For example, in contrast to the above-described embodiment in which first tube rack 11 can be moved only vertically and second tube rack 12 can be moved horizontally and vertically, modifications may be made so that these tube racks can be moved in the opposite way or both of them can be moved horizontally and vertically.

As is evident from the above description, the present invention enables extranuclear gene DNA (plasmid DNA)

replicated and amplified by transformants to be extracted and purified from a large number of overnight culture samples in a short period of time without using a centrifugal separator. Moreover, since the extraction and purification of DNA is carried out by suction through filters, highly pure plasmid DNA can be obtained at low cost.

We claim:

1. Apparatus for the extraction and purification of DNA, comprising:

a first tube rack having disposed therein at least one first filter tube for the extraction and purification of DNA;

a second tube rack having disposed therein at least one second filter tube for the extraction and purification of DNA;

a vacuum device for applying suction to the filters included in said first and second filter tubes;

a first transfer device for moving said first tube rack vertically;

a second transfer device for moving said second tube rack vertically;

a third transfer device for moving at least one of said first and second tube racks horizontally; and control means for controlling said first, second, and third transfer devices and said vacuum device.

2. An apparatus according to claim 1, further comprising a recovery vat that can be brought into airtight contact with the bottom of said second tube rack to define a vacuum chamber by the bottom of said first or second tube rack and said recovery vat.

3. An apparatus according to claim 2, further comprising a recovery rack detection sensor for determining whether a recovery rack for holding at least one recovery tube is disposed in said recovery vat.

4. An apparatus according to claim 1, wherein at least one of said first and second tube racks is provided with a passage extending through the bottom wall and inner side wall thereof, and said first and second tube racks can be laid one on top of the other to define a vacuum chamber therebetween.

5. An apparatus according to claim 1, further comprising at least one tube detection sensor for judging whether or not said first and second filter tubes are disposed in said first and second tube racks according to predetermined protocol.

6. An apparatus according to claim 1, wherein said first filter tube includes at least a trap filter and a membrane filter, and said second filter tube includes at least a glass fiber filter, a glass powder layer and a membrane filter.

7. Apparatus for the extraction and purification of DNA, comprising:

a first tube rack having disposed therein at least one first filter tube for the extraction and purification of DNA;

a second tube rack having disposed therein at least one second filter tube for the extraction and purification of DNA;

a vacuum device for applying suction to the filters included in said first and second filter tubes;

at least one transfer device for moving each of said first and second tube racks vertically and for moving at least one of said first and second tube racks horizontally; and a controller operably associated with said transfer device and said vacuum device for controlling said transfer device and said vacuum device.

8. An apparatus according to claim 7, further comprising a recovery vat that can be brought into airtight contact with the bottom of said second tube rack to define a vacuum chamber by the bottom of said first or second tube rack and said recovery vat.

9. An apparatus according to claim 7, wherein at least one of said first and second tube racks is provided with a passage extending through the bottom wall and inner side wall thereof, and said first and second tube racks can be laid one on top of the other to define a vacuum chamber therebetween.

* * * * *

UNITED STATES PATENT AND TRADEMARK OFFICE
CERTIFICATE OF CORRECTION

PATENT NO. : 5,645,723
DATED : July 8, 1997
INVENTOR(S) : Fujishiro et al.

It is certified that error appears in the above-indentified patent and that said Letters Patent is hereby corrected as shown below:

```
Title page, Item [56]:
Column 2, line 4, "Ferwood" should be --Fernwood--.

Column 2, line 6, "Sköjd" should be --Sköld--.

Column 2, line 7, "William" should be --Williams--.

Column 2, insert --4,931,402   6/1990    Abplanalp--.

Column 3, line 30, "piper" should be --pipet--.

Column 4, line 33, "50 dis" should be --50d is--.

Columns 5-8, level numerals should not be bold type.
```

Signed and Sealed this

Seventh Day of July, 1998

*Attest:*

BRUCE LEHMAN

*Attesting Officer*    *Commissioner of Patents and Trademarks*